United States Patent
Hasselbach et al.

(10) Patent No.: US 9,403,764 B2
(45) Date of Patent: Aug. 2, 2016

(54) METHOD OF PRODUCTION OF A METHIONINE SALT

(71) Applicants: Hans Joachim Hasselbach, Gelnhausen (DE); Martin Koerfer, Kahl (DE); Christof P. Gruener, Mobile, AL (US); Franz H. Hanrath, Mobile, AL (US); Juergen Stock, Frankfurt (DE); Jignesh Gangadwala, Mobile, AL (US); Horst Krull, Hanau (DE)

(72) Inventors: Hans Joachim Hasselbach, Gelnhausen (DE); Martin Koerfer, Kahl (DE); Christof P. Gruener, Mobile, AL (US); Franz H. Hanrath, Mobile, AL (US); Juergen Stock, Frankfurt (DE); Jignesh Gangadwala, Mobile, AL (US); Horst Krull, Hanau (DE)

(73) Assignee: EVONIK DEGUSSA GmbH, Essen (DE)

(*) Notice: Subject to any disclaimer, the term of this patent is extended or adjusted under 35 U.S.C. 154(b) by 0 days.

(21) Appl. No.: 14/638,870

(22) Filed: Mar. 4, 2015

(65) Prior Publication Data

US 2015/0175535 A1 Jun. 25, 2015

Related U.S. Application Data

(62) Division of application No. 13/597,816, filed on Aug. 29, 2012, now Pat. No. 9,023,284.

(60) Provisional application No. 61/529,013, filed on Aug. 30, 2011.

(51) Int. Cl.
| | |
|---|---|
| *C07C 319/20* | (2006.01) |
| *C07D 233/76* | (2006.01) |
| *B01J 19/24* | (2006.01) |
| *B01D 3/00* | (2006.01) |

(52) U.S. Cl.
CPC .............. *C07C 319/20* (2013.01); *B01D 3/009* (2013.01); *B01J 19/24* (2013.01); *C07D 233/76* (2013.01)

(58) Field of Classification Search
CPC ..... C07C 319/20; C07C 323/58; C07D 233/76
See application file for complete search history.

(56) References Cited

U.S. PATENT DOCUMENTS

| | | | |
|---|---|---|---|
| 5,770,769 A | 6/1998 | Geiger et al. | |
| 5,990,349 A | 11/1999 | Geiger et al. | |
| 6,126,972 A | 10/2000 | Körfer et al. | |
| 6,140,536 A | 10/2000 | Hasseberg et al. | |
| 6,150,563 A | 11/2000 | Hasselbach et al. | |
| 6,287,627 B1 | 9/2001 | Binder et al. | |
| 6,797,827 B2 | 9/2004 | Körfer et al. | |
| 7,119,228 B2 | 10/2006 | Buss et al. | |
| 7,179,938 B2 | 2/2007 | Weckbecker et al. | |
| 7,199,270 B2 | 4/2007 | Möller et al. | |
| 7,655,072 B2 * | 2/2010 | Hasselbach ............ | B01D 53/62 423/242.2 |
| 7,833,508 B2 | 11/2010 | Redlingshöfer et al. | |
| 9,029,597 B2 * | 5/2015 | Steffan .................. | C07C 319/20 422/187 |
| 2006/0016334 A1 | 1/2006 | Hasselbach et al. | |
| 2009/0018370 A1 | 1/2009 | Fukuoka et al. | |
| 2012/0165573 A1 | 6/2012 | Finkeldel et al. | |
| 2012/0215021 A1 | 8/2012 | Buss et al. | |
| 2012/0215022 A1 | 8/2012 | Buss et al. | |
| 2013/0245318 A1 | 9/2013 | Steffan et al. | |

FOREIGN PATENT DOCUMENTS

| | | | | |
|---|---|---|---|---|
| CN | 101370758 A | 2/2009 | | |
| EP | 0 780 370 A2 | 6/1997 | | |
| EP | 1 978 007 A1 | 10/2008 | | |
| EP | 1978007 A1 * | 10/2008 | ............. | B01D 3/009 |
| JP | 8-502277 A | 3/1996 | | |
| JP | 3990475 B2 | 10/2007 | | |
| JP | 4881299 B2 | 2/2012 | | |
| JP | 2014-529616 A | 11/2014 | | |

OTHER PUBLICATIONS

Combined Office Action and Search Report issued Feb. 23, 2015 in Chinese Patent Application No. 201280042636.1 (submitting English translation only).
Office Action issued Mar. 9, 2015 in Japanese Patent Application No. 2014-527590 (submitting English translation only).
"Factory Operation Series" Expanded Edition, Distillation, 1992, pp. 59-70.
International Search Report and Written Opinion issued Sep. 13, 2013 in PCT/EP2012/066375.

* cited by examiner

*Primary Examiner* — Yong Chu
(74) *Attorney, Agent, or Firm* — Oblon, McClelland, Maier & Neustadt, L.L.P.

(57) ABSTRACT

A method for production of a methionine salt in a reactive rectification column containing a weir having a height of 100 mm or more is provided.

13 Claims, 3 Drawing Sheets

METHOD OF PRODUCTION OF A METHIONINE SALT

CROSS REFERENCE TO RELATED APPLICATIONS

This application is a divisional application of prior U.S. application Ser. No. 13/597,816, now U.S. Pat. No. 9,023,284, filed Aug. 29, 2012, the disclosure of which is incorporated herein by reference in its entirety. The parent Application claims priority to U.S. Non-provisional Application No. 61/529,013, filed Aug. 30, 2011, the disclosure of which is incorporated herein by reference in its entirety.

BACKGROUND OF THE INVENTION

1. Field of the Invention

The invention relates to a method of production of a methionine salt, in particular the production of a methionine salt starting from the precursors 3-methylmercaptopropionaldehyde (MMP) and hydrogen cyanide (HCN) or starting from at least one component that can be prepared from these raw materials, such as methylmercaptopropionaldehyde-cyanohydrin (MMP-CN). In particular the invention relates to the alkaline hydrolysis of 5-(2-methylmercapto)-hydantoin in a column. The invention further relates to a reaction system suitable for this method, comprising a reactive-rectification column, and the use of the reaction system.

2. Discussion of the Background

The industrial synthesis of racemic methionine (mixture of 50% L-methionine and 50% D-methionine) starts from petrochemical raw materials, in particular propene, sulphur, methane and ammonia. According to usual methods, the precursor 3-methylmercaptopropionaldehyde is thus prepared via the precursors acrolein, methylmercaptan and hydrogen cyanide. Then this aldehyde is converted with ammonia, carbon dioxide and hydrogen cyanide to 5-(2-methylmercapto)-hydantoin, alkaline hydrolysis of which leads to an alkali salt of methionine. Neutralization with an acid such as carbon dioxide or sulphuric acid gives racemic methionine, several hundred thousand tonnes of which are produced annually.

A conventional method is based on the use of circulated alkaline potassium salts for hydrolysis of 5-(2-methylmercapto)-hydantoin. Unwanted by-products lead to neutral potassium salts, which are then no longer available to the alkaline hydrolysis reaction. These must be removed from the potassium-containing circulating solution. The associated potassium losses must be compensated by using KOH. Another side reaction leads to the formation of 4-methylmercapto-2-hydroxybutanoic acid and therefore to a loss of yield. 4-Methylmercapto-2-hydroxybutanoic acid is also present as neutral potassium salt in the bottoms product of reactive distillation and therefore disturbs the circulation of alkaline potassium. This by-product is therefore unsuitable for supporting the hydrolysis of 5-(2-methylmercapto)-hydantoin and must be removed from the potassium circuit, which is associated with further losses of raw materials.

It is known from the background art that methionylmethionine (also called methionine dipeptide) is a by-product in methionine production by hydrolysis of hydantoin (e.g. EP 2 133 329 A2, EP 0839 804 B1) and forms in the following way (formula I).

A two-stage hydantoin hydrolysis for reducing the formation of methionine dipeptide is described in EP 2 133 329 A2. In this, the first stage takes place in a flow tube with gas outlet and the second stage in a stirred reactor, with total residence times of 20-60 minutes. This gives a product distribution of 91 mol. % methionine and 9 mol. % methionine dipeptide. The high proportion of methionine dipeptide is very unfavourable and requires further process steps to reduce losses of yield. Thus, EP 2 186 797 A1 describes expensive heat treatment at 150-200° C. of the concentrates of the mother liquors from methionine crystallization, to cleave methionine dipeptide hydrolytically back to methionine. For this, after crystallization, which takes place at 20° C., the mother liquor must be heated again to the required high temperatures, which is energetically unfavourable.

JP 2006-206534 A describes the depletion of $NH_3$ from a process solution produced in an additional process step by hydrolysis of hydantoin at normal pressure and therefore at about 100° C. by means of a plate column. This is a normal distillation of $NH_3$, having no effect on the hydrolysis reaction. A drawback of this procedure is that the $NH_3$ thus removed is no longer available for hydantoin synthesis. Moreover, the solution thus treated is heavily diluted, as stripping steam at a pressure of 5 bar (excess) (corresponding to 158° C.) is used, which is disadvantageous for further processing.

EP-A-1710232 and EP-A-1256571 describe a method of production of D,L-methionine from 5-(2-methylmercapto)-hydantoin, wherein the process stages 5-(2-methylmercaptoethyl)-hydantoin formation and methioninate formation (alkaline hydrolysis) can be operated continuously and integrated successively in a fully continuous process. How a column for hydrolysis of Met-hydantoin should be designed technically to minimize by-product formation has not yet been described in the background art. Furthermore, there is no description of how the $NH_3$ circuit between hydantoin formation and hydantoin hydrolysis is to be operated loss-free at minimized energy expenditure. The hydrolysis process can be carried out in a steam-heated column, wherein the 5-(2-methylmercaptoethyl)-hydantoin solution is advantageously fed continuously to the top of the column at a rate such that the hydrolysis product, potassium methioninate solution, can accordingly be withdrawn at the bottom of the column after quantitative hydrolysis. The mother liquor can be reused after separating the methionine solids. The gaseous constituents (steam, ammonia and carbon dioxide) can be discharged at the top of the column and can be used for restoration of the aqueous ammonia/carbon dioxide solution for production of 5-(2-methylmercaptoethyl)-hydantoin. It is described as being especially advantageous, for avoiding by-products, to carry out the hydrolysis right at the start in the presence of alkali and carbon dioxide, i.e. in particular there is a mixture of alkali compounds, in particular alkali hydrogen carbonate, alkali carbonate, alkali hydroxide. To achieve complete conversion of the valuable starting material MMP to hydantoin, a molar ratio of 1.005-1.02 mol/mol HCN/MMP is employed in the method described. As a result of hydrolysis of unreacted hydrogen cyanide, in the column there is production of $NH_3$ by the following reaction (formula II):

$$HCN + 2H_2O \rightarrow NH_3 + HCOOH \qquad \text{II}$$

The resultant formic acid is located as non-volatile potassium formate at the bottom of the reaction column; it thus displaces the required alkaline carbonates and therefore disturbs the alkaline potassium circuit.

SUMMARY OF THE INVENTION

The problem to be solved by the invention was therefore to provide an improved method, relative to the background art, for producing a methionine salt starting from the raw materials methylmercaptopropionaldehyde and hydrogen cyanide or starting from at least one compound that can be prepared from these raw materials, such as methylmercaptopropionaldehyde-cyanohydrin.

The problem is solved by the reaction system according to the invention, use thereof according to the invention and the method according to the invention.

In one embodiment, the present invention relates to a reaction system, comprising:
a reactive rectification column comprising
a weir having a height of 100 mm or more;
wherein said reaction system is suitable for production of a methionine salt.

In another embodiment, the present invention relates to a method for continuous production of a methionine salt, comprising:
reacting 3-methylmercaptopropionaldehyde and hydrogen cyanide or a component that can be produced therefrom, thereby obtaining a solution containing 5-(2-methylmercaptoethyl)-hydantoin;
alkaline hydrolysing the 5-(2-methylmercaptoethyl)-hydantoin to a methionine salt in a reactive rectification column, wherein only the solution containing 5-(2-methylmercaptoethyl)-hydantoin is fed on a topmost plate of the reactive rectification column and an alkaline circulating solution is fed on a plate located under the topmost plate.

DETAILED DESCRIPTION OF THE INVENTION

The ranges stated below include all values and subvalues between the upper and lower limit of the ranges.

The reaction system has the following features:
1. Reaction system for production of a methionine salt, comprising a reactive-rectification column with a weir height of 100 mm or more
2. Reaction system according to 1, wherein
   the weir height is in the range from 100 to 1000 mm, preferably in the range from 150 to 700 mm,
   the plate spacing is in the range from 500 to 1000 mm,
   the ratio of column diameter to weir length is in the range from 1.1 to 1.3,
   the ratio of the cross-sectional area to the area through which gas flows is in the range from 1.5 to 2 and
   the number of plates is in the range from 15 to 25, preferably in the range from 18 to 20.
3. Reaction system according to 1 or 2, wherein the reactive-rectification column is a sieve plate column, perforated plate column, valve plate column or bubble plate column.
4. Reaction system according to 3, wherein, in the reactive-rectification column the ratio total area of all holes/area through which gas flows is in the range from 0.04 to 0.08 and
   the diameter of the individual holes in the sieve plate is in the range from 5 to 10 mm.
5. Reaction system according to one of the above numbers, wherein the weir heights ensure an average residence time of the respective mixture of less than 0.5 min per plate.
6. Reaction system, wherein the reaction system further comprises at least one reactive absorber and optionally a second reactor for the production of 5-(2-methylmercaptoethyl)-hydantoin.
7. Reaction system according to 5, wherein the reactive absorber is a jet washer system.
8. Reaction system according to one of the numbers 1 to 7, wherein zirconium is used in the reactive-rectification column and/or in the reactive absorber and/or in the second reactor as material for parts in contact with the product.

The method has the following features:
1. Method for continuous production of a methionine salt, wherein the following steps are carried out:
   reaction of 3-methylmercaptopropionaldehyde and hydrogen cyanide or of a component that can be produced therefrom, wherein a solution containing 5-(2-methylmercaptoethyl)-hydantoin is obtained;
   alkaline hydrolysis of the 5-(2-methylmercaptoethyl)-hydantoin obtained to a methionine salt in a reactive-rectification column, wherein only the solution containing 5-(2-methylmercaptoethyl)-hydantoin is fed on the topmost plate of the reactive-rectification column and an alkaline circulating solution is fed on a plate under that, preferably on the 2nd plate from the top.
2. Method according to 1, wherein the alkaline circulating solution contains an alkali carbonate, preferably potassium carbonate.
3. Method according to 1 or 2, wherein water, ammonia and $CO_2$ are removed from the top of the reactive-rectification column and the $NH_3$ removed is condensed completely or partially for use in the synthesis of 5-(2-methylmercaptoethyl)-hydantoin.

4. Method according to one of the numbers 1 to 3, wherein the concentration of ammonia in the bottom of the rectification column is less than 120 ppm, preferably less than 100 ppm and most preferably less than 80 ppm.
5. Method according to one of the numbers 1 to 4, wherein the conversion to 5-(2-methylmercaptoethyl)-hydantoin is carried out in a reactive absorber and then in a second reactor, preferably in a second reactor designed as a flow tube.
6. Method according to one of the numbers 1 to 5, wherein the temperature of the reaction mixture at the outlet of the reactive-rectification column is in the range from 180° C. to 190° C.
7. Method according to one of the numbers 1 to 6, wherein the temperature of the gas phase at the top of the reactive-rectification column is in the range from 160° C. to 170° C.
8. Method according to one of the above numbers 1 to 7, wherein alkaline hydrolysis is carried out at a pressure in the range from 8 bar (excess) to 10 bar (excess).
9. Method according to one of the numbers 1 to 8, wherein steam is used as heating and stripping medium in the reactive-rectification column.
10. Method according to one of the numbers 1 to 9, wherein the method is carried out in a reaction system according to one of the numbers 1 to 8.

The invention also relates to the use of the reaction system for the production of methionine.

Reference is made expressly to the preferred embodiments of the invention presented in the specification.

The invention relates to a method for continuous production of a methionine salt, wherein 3-methylmercaptopropionaldehyde and hydrogen cyanide (HCN) or a component that can be produced therefrom are reacted, wherein a solution containing 5-(2-methylmercaptoethyl)-hydantoin is obtained and wherein an alkaline hydrolysis of the 5-(2-methylmercaptoethyl)-hydantoin obtained to a methionine salt is carried out in a reactive-rectification column, wherein only the solution containing 5-(2-methylmercaptoethyl)-hydantoin is fed on the topmost plate of the reactive-rectification column and an alkaline circulating solution is fed on a plate located under that, preferably on the 2nd plate from the top. The alkaline circulating solution preferably contains an alkali carbonate, preferably potassium carbonate.

The reaction of the components 3-methylmercaptopropionaldehyde, hydrogen cyanide and ammonia and carbon dioxide, or of components from which the aforementioned components can be produced, to 5-(2-methylmercaptoethyl)-hydantoin takes place optionally in the presence of water. In order to achieve conversion of methylmercaptopropionaldehyde that is as complete as possible, the starting substances hydrogen cyanide and methylmercaptopropionaldehyde are preferably used in the molar ratio of 1.005-1.02 mol/mol HCN/MMP.

Preferred starting substances for the production of 5-(2-methylmercaptoethyl)-hydantoin (also called hydantoin derivative or hydantoin for short) are 3-methylmercaptopropionaldehyde, hydrogen cyanide, ammonia and carbon dioxide. By-products of this reaction are the components 5-(2-methylmercaptoethyl)-hydantoic acid amide, 5-(methylmercaptoethyl)-hydantoic acid, methionine amide and in traces, along with other components, 3-methylmercaptopropionaldehyde cyanohydrin. These can be converted to methionine in alkaline hydrolysis, just like the main product. An exception is 3-methylmercaptopropionaldehyde cyanohydrin, which on hydrolysis is converted to 4-methylmercapto-2-hydroxybutanoic acid. The precise composition of the product mixture produced in the hydantoin reaction can be elucidated by HPLC.

5-(2-methylmercapto)-hydantoin

5-(2-methylmercapto)-hydantoic acid amide 5-(2-methylmercapto)-hydantoic acid methionine amide

3-methylmercaptopropionaldehyde-cyanohydrin

For complete conversion of MMP to the hydantoin derivative, it is advantageous if MMP and $NH_3$ are used in the reactive absorber in a molar ratio of about 1 to 3, wherein the basic equation of hydantoin synthesis has the following appearance (formula III):

As can be seen from formula IV, $CO_2$ as reaction partner is always present in excess, because during formation of the methionine-potassium salt, additionally 0.5 mol $CO_2$ is released from potassium carbonate.

It is also favourable, for selective reaction of MMP with $NH_3$, HCN and $CO_2$ in aqueous phase to hydantoin, if the reaction partners are mixed thoroughly at the moment when they come together. It is therefore preferable to use a jet washer system as reactive absorber. The amount of circulated process solution is then preferably 18 to 22 times, especially preferably 20 times the total of the amounts of MMP and HCN used. The jet washer ensures very good mass transfer from the gas phase into the liquid phase.

To achieve complete conversion of MMP to hydantoin in a reaction time that is acceptable for industrial use, the hydantoin reaction mixture leaves the jet washer, and is led through a second reactor, which is designed as a flow tube, wherein the residence time in the flow tube is about 10 minutes. For maximum hydantoin yield, it is important in particular to avoid formation of the by-product 4-methylmercapto-2-hydroxybutanoic acid (=methionine-hydroxy analogue, MHA), which occurs if the residence time is insufficient (formula V):

In the post-reaction phase in the reaction tube, the losses through formation of 4-methylmercapto-2-hydroxybutanoic acid can be reduced to less than 1 mol. % relative to the MMP used (detection by HPLC).

Alternatively, in hydantoin production it is also possible to use previously synthesized MMP-cyanohydrin.

In a subsequent step, the hydantoin derivative is converted in alkaline hydrolysis to methionine. Methionine denotes racemic methionine, which is also designated as D,L-methionine. This step of the method according to the invention is preferably carried out in a sieve plate column, which is operated as reactive distillation.

The reactive distillation column that is operated in the method of the invention, and is preferably equipped with sieve plates, brings about—along with very effective distillation of the ammonia—mainly a very advantageous reaction for alkaline hydrolysis of hydantoin with formation of the potassium salt of methionine. This takes place according to formula IV shown above.

Furthermore, the invention offers the advantage that the amount of $NH_3$ required for operation of the reactive distillation-reactive absorber coupled system does not have to be prepared and fed in separately, but is circulating in the system. The concentration of ammonia in the bottoms product is preferably less than 120 ppm, more preferably less than 100 ppm and most preferably less than 80 ppm. This manner of operation means that it is advantageously possible in the "steady state" to dispense with external $NH_3$ feed completely.

It has been found that when hydantoin hydrolysis is carried out in reactive distillation designed as a sieve plate column, several advantageous effects can be achieved.

The inventors' own intensive research into the reaction mechanism of hydantoin hydrolysis showed, surprisingly, that first there is formation of a stable intermediate, namely the potassium salt of hydantoic acid, according to the following equation (formula VI).

The further hydrolytic degradation of hydantoic acid takes place according to the following equation (formula VII):

As the potassium salt that has formed can react via the equilibrium reaction back to the salt of hydantoic acid, for conversion that is as complete as possible, with short reaction times as are required industrially, it is a considerable advantage if ammonia and $CO_2$ are removed effectively from the liquid phase during the reaction. A sieve plate column is used for this in one embodiment. For controlling a stable $NH_3$ holdup in the reactive distillation-reactive absorber system of the invention, in a further embodiment a small partial stream is deliberately taken from the gaseous top product and discarded. In this way, the excess $NH_3$ that forms can be removed from the system in an environment-friendly manner and avoiding loss of valuable raw materials.

According to the invention, preferably water, ammonia ($NH_3$) and $CO_2$ are distilled off at the top and then all of the $NH_3$ or a proportion thereof is condensed and used in hydantoin synthesis, which is preferably designed as a reactive absorber, especially preferably as a reactive absorber that is operated without losses of $NH_3$ in the waste gas. The stream from the bottom of the reactive distillation system contains the alkali salt, preferably the potassium salt of methionine, which is processed further to methionine as is known in the background art.

The heating and stripping medium used is preferably steam, which is fed in under pressure below the bottommost sieve plate. The amount, velocity and temperature of the stream of steam are preferably controlled in such a way that a temperature of 180° C.-190° C. is reached at the outlet of the reactive distillation column, whereas the gas phase leaves at the top of the column at a temperature of 160° C.-170° C. This temperature range corresponds to a pressure range of 8-10 bar (excess). Furthermore, the amount of steam depends on the desired throughputs.

The invention further relates to a reaction system for the production of methionine salt, which comprises a reactive-rectification column with a weir height of 100 mm or more (also called reactive distillation column or reactive distillation).

Figure 1:
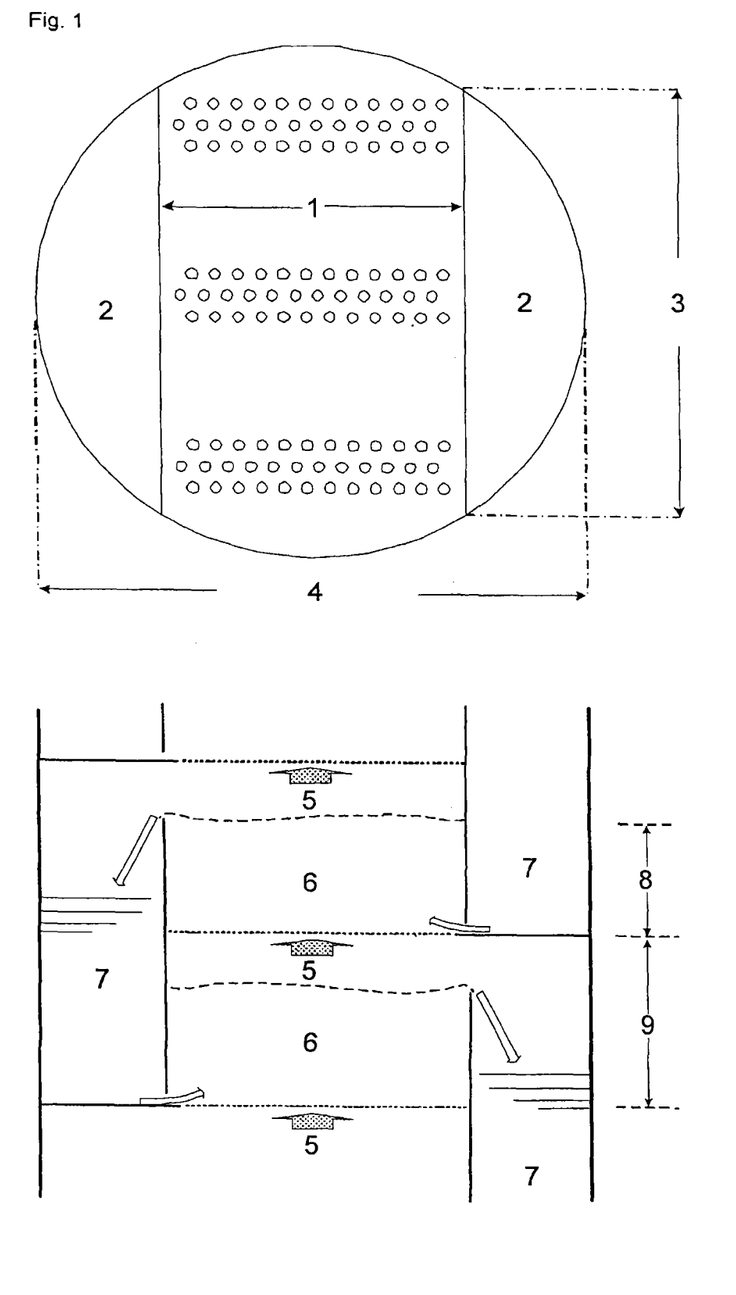
FIG. 1, top, shows a schematic top view of a sieve plate and, bottom, in one section, the side view of a column of a preferred embodiment.

A preferred embodiment has the following design features (see FIG. 1):

Weir height 8: 100-1000 mm, preferably 150-700 mm
Plate spacing 9: 500-1000 mm
Ratio: column diameter 4/weir length 3: 1.1-1.3
Ratio: cross-sectional area/area through which gas flows: 1.5-2
Number of plates: 15-25, especially 18-20.

The cross-sectional area can be calculated from the column diameter 4. The area through which gas flows is found by subtracting the areas of the two downcomers 2 from the cross-sectional area.

Figure 2:
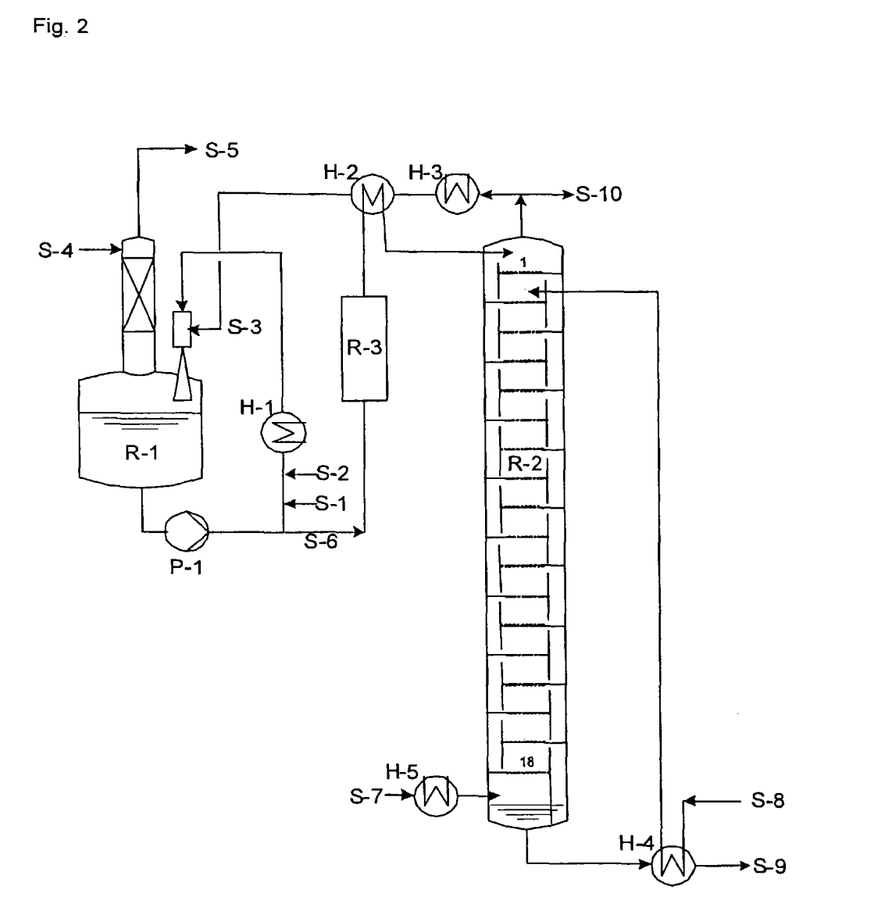
FIG. 2 shows a flow chart of a plant including a sieve plate column according to an embodiment of the invention.

If the column is a sieve plate column (see FIGS. 1 and 2), the following features are preferred:

Ratio: total area of all holes/area through which gas flows: 0.04-0.08 Diameter of the individual holes in the sieve plate 5-10 mm.

FIG. 1, top, shows a schematic top view of a sieve plate and, bottom, in one section, the side view of a column of a preferred embodiment. The side view shows the vapour phases 5, liquid/vapour phases 6 and the liquid phases 7 on the individual plates.

The plate spacing can preferably be adjusted to the different reaction phases in the column. In one embodiment, in the top half of the column the plate spacing and the weir heights are preferably kept small, to speed up the stripping of $NH_3$ and $CO_2$, whereas in the bottom half the plate spacing and weir heights are larger, for completing the conversion with a longer residence time.

In a preferred embodiment the weir height for the upper plates of a column is in the range from 100 to 200 mm, preferably 150 mm, at a plate spacing in the range from 800 to 1000 mm, preferably 1000 mm, and the weir height for the middle plates is in the range from 400 to 600 mm, preferably 500 mm, at a plate spacing in the range from 700 to 900 mm, preferably 800 mm, and the weir height for the bottom plates is in the range from 600 to 800 mm, preferably 700 mm, at a plate spacing in the range from 800 to 1000 mm, preferably 1000 mm. The plate spacing is in each case measured from one plate to the plate above it. In the case of columns with 15 to 17 plates, preferably plates 1 to 4 count as the top plates, plates 5 to 11 as the middle plates and the lower plates count as the bottom plates. In the case of columns with 18 to 21 plates, preferably plates 1 to 5 count as the top plates, plates 6 to 12 as the middle plates and the lower plates count as the bottom plates. In the case of columns with 22 to 25 plates, preferably plates 1 to 7 count as the top plates, plates 8 to 16 as the middle plates and the lower plates as the bottom plates.

The preferred combination of reactive-rectification column and reactive absorber permits, uniquely, the provision of process conditions that make the production of methionine quite particularly economically attractive.

The reactive-rectification column can have sampling points on one or more or all plates. Preferably it has sampling points on every fourth, every third, every second to fourth or third, especially preferably on every second plate. The samples taken are preferably allowed to cool and are analysed for hydantoin, hydantoic acid, methionine, methionyl-methionine by high-performance liquid chromatography (HPLC). The $NH_3$ content can be determined potentiometrically by means of an ion-selective electrode.

It is found in particular that it is possible to operate the preferred embodiment of reactive distillation equipped with sieve plates (see FIG. 1) with an amount of steam of less than 0.25 t steam per t process solutions, fed at the top of the column. This is completely unexpected, because at the high pressures in reactive distillation described above and the aforementioned large $NH_3$ circulation from the top of reactive distillation of about 0.4 t $NH_3$ per t of MMP employed, much larger $NH_3$ losses via the bottom of the column were to be expected. A lower limit is imposed for the amount of steam used when the so-called weep point of the sieve plates is reached. This is understood as the effect that starting from a certain reduced gas flow from below, liquid is increasingly discharged (weeps) directly through the holes of the sieve plates and no longer takes the intended path via the downcomers 2. As a result, the residence time for the hydrolysis reaction would be lost and thus the desired function of reactive distillation would be disturbed. In detailed studies of the present reaction system it was determined that the weep point is equal to 50% of the specific amount of steam stated above. The preferred amounts of steam are in the range from 0.13 t steam per t process solution to 0.4 t steam per t process solution, most preferably in the range from 0.20 t steam per t process solution to 0.25 t steam per t process solution.

In a preferred embodiment, zirconium is used in the reactive distillation and/or in the reactive absorber and/or in the second reactor as material for the parts in contact with the product. As a result, corrosion damage to the parts in contact with the product can be avoided sustainably. The process combination of reactive distillation and reactive absorption disclosed here proves particularly advantageous, against the background that zirconium is a high-cost material, because the close coupling of the two process steps minimizes the number and length of connecting pipelines and the number of buffer tanks. Accordingly, the method of the invention is on the whole very sustainable, as it avoids the discharge of environmentally harmful heavy metals such as chromium and nickel due to corrosion. Furthermore, the close coupling of the process steps means that the waste heat resulting from operation of the column can be utilized ideally for warming the feed streams and additionally for operation of the evaporating unit.

The reaction system according to the invention ensures a sufficient residence time of the reaction partners in the column. At the same time, in view of the high costs of the material zirconium, it is advantageous if the number of plates can be kept small. The plates are preferably sieve plates. Other usual plate designs (e.g. slotted, valve or bubble-cap plates) can be used, but they have the disadvantage that manufacture thereof from the material zirconium is very difficult. Therefore in this application reference is made to sieve plates and sieve plate columns. The invention is not, however, limited to these, but relates equally to slotted, valve or bubble-cap plates or slotted, valve or bubble-cap plate columns, unless expressly stated otherwise.

In one embodiment the reactive distillation column provides quantitative hydrolysis of hydantoin at temperatures between 160° C. and 180° C. in the pressure range 8 bar (excess) to 10 bar (excess) in a residence time of less than 10 minutes, wherein the column ensures an average residence time of less than 0.5 minute per plate. The weir height has an important influence on the residence time of the individual sieve plate (see FIG. 1). It was found, surprisingly, that far larger weir heights are possible in the reaction system of the invention than those described in the background art (see e.g. Mersmann, Thermische Verfahrenstechnik (Thermal process engineering), p. 222, Springer Verlag, 1980). Weir heights up to max. 60 mm are stated in the latter, whereas weir heights up to 1000 mm are used in the invention. Therefore in a preferred embodiment the use of zirconium as material is minimized, while simultaneously reducing the $NH_3$ concentration at column outlet to less than 100 ppm.

The mother liquor from precipitation of the methionine salt is preferably used for the alkaline hydrolysis of hydantoin. The mother liquor contains the potassium salts mainly as $KHCO_3$. This is then preferably concentrated, to remove $CO_2$ and water, which leads to a solution with high potassium carbonate content and therefore increased basicity, which is advantageous for the hydrolysis reaction.

The energy required for operation of this evaporation step can be obtained in an especially suitable manner from the waste heat of the reactive distillation-reactive absorption combination. In a preferred embodiment, the amount of water that is required for production of the amounts of steam necessary for operation of the reactive distillation is obtained from the condensate of the evaporation step. In this way the complete methionine production process can be operated largely without generating wastewater, which represents a considerable advantage from the environmental standpoint.

According to the method of the invention, for alkaline hydrolysis, the reaction solutions are introduced into the reactive-rectification column in such a way that only the solution containing 5-(2-methylmercaptoethyl)-hydantoin is fed in at the topmost plate and the alkaline circulating solution is fed on a plate located under that, preferably on the 2nd plate from the top (see FIG. 2). Therefore first preferably $NH_3$, $CO_2$ and HCN are stripped from the hydantoin solution and recycled to the hydantoin reaction. As a result, in particular the loss of HCN according to formula II is minimized and at the same time formation of potassium formate is avoided. Potassium formate, as a neutral salt, is not suitable for supporting the hydrolysis of hydantoin and must therefore be extracted from the potassium circuit. The associated losses of potassium must be made up using KOH. The sequential feed of hydantoin solution and alkaline circulating solution at the top of the reactive distillation column therefore avoids costs for raw materials and waste disposal.

In a preferred embodiment, using a reactive distillation column with sieve plates, advantageously the formation of by-products such as methionine dipeptide is suppressed. Since formation of methionine dipeptide requires the simultaneous presence of the starting compound hydantoin and the potassium salt of methionine, efficient separation of the reaction partners is advantageous for avoiding this reaction. This takes place in an especially suitable manner in a reactive distillation equipped with sieve plates, as remixing is largely prevented in this system. However, the invention is not restricted to this, but relates equally to slotted, valve or bubble-cap plates or slotted, valve or bubble-cap plate columns, unless expressly stated otherwise. In this way, the proportions present in the hydrolysed reaction mixture are 98 mol. % Met and 2 mol. % Met-dipeptide, wherein a residence time of less than 10 minutes is required.

The preferred method of the invention of alkaline hydantoin hydrolysis in a sieve plate column minimizes the formation of the by-product Met-dipeptide by exploiting two synergistic effects. On the one hand, the plate design largely prevents remixing and as a result formation of Met-dipeptide is inhibited, and on the other hand the intensive stripping operation increases the basicity in the reaction solution, as shown by the following reaction equation.

$$CO_3^{2-} + H_2O \rightarrow 2OH^- + CO_2, gas \qquad\qquad VIII$$

An increased proportion of base in its turn accelerates cleavage of the resultant Met-dipeptide. The mechanism is shown in formula IX:

This explains how the multi-stage sieve plate column of the invention both minimizes Met-dipeptide formation and supports the hydrolytic degradation of the dipeptide, which overall greatly reduces the losses associated with by-product formation and disposal thereof.

The presence of a sufficient amount of non-volatile basic compounds in the reaction matrix is important for efficient conversion of hydantoin to methionine in the column of the invention. These are potassium salts, such as KOH, potassium carbonate, potassium hydrogen carbonate, potassium-methionine, potassium salt of Met-dipeptide. As these potassium salts are very largely recycled, but at the same time potassium salts of strong acids are also formed in side reactions (formula II and formula V), it is important to monitor the basicity in the potassium circuit and keep it stable.

In the continuous process of the invention it is therefore important to determine the basicity, in particular at column outlet. For this, a sample is taken and after it has cooled to ambient temperature it is submitted to classical acid-base titration with an acid as titrant, wherein the titration end point is found between pH 4 and 5. Preferably the basicity values in the reaction matrix at the end of the reaction are in the range from 2.2-2.8 mol base per kg saponified solution, preferably 2.5 mol base/kg saponified solution. Lower basicities lead to increased Met-dipeptide formation and higher $NH_3$ concentrations in the saponified product. Higher basicity values mean that, relative to the amount of Met produced, increased circulation of alkaline potassium salts is required in the process. This is energetically increasingly costly and therefore counterproductive.

Having generally described this invention, a further understanding can be obtained by reference to certain specific examples which are provided herein for purposes of illustration only, and are not intended to be limiting unless otherwise specified.

EXAMPLES

Example 1

FIG. 2 provides further explanation of the invention.

The production of hydantoin took place in the reaction system R-1. The raw materials HCN and MMP were mixed via the feed points S-1 and S-2 with about 20-times the amount of hydantoin reaction solution, which was circulated by pump P-1. Heat exchanger H-1 served for abstraction of heat and maintains the reactor contents R-1 preferably at a temperature of 100° C.-120° C. Alternatively, a premix of MMP and HCN or separately produced MMP-cyanohydrin could also be fed into the stream circulated by pump P-1. The resultant combined stream then served as the driving jet in a jet mixer, which brought the partially condensed low-boiling fractions (S-3) from the top of the reactive distillation R-2 intensively into contact with the hydantoin process solution and returned them to reactor R-1. Via stream S-5, which was washed with water (S-4) until $NH_3$-free, a $CO_2$-containing stream left the reactor R-1. This $CO_2$ stream arose because according to formula IV, in hydantoin hydrolysis in the presence of potassium carbonate, stoichiometrically 0.5 mol more $CO_2$ forms per mol of methionine formed than was required for hydantoin formation according to formula III. The resultant $NH_3$-free $CO_2$-stream was, as described in U.S. Pat. No. 7,655,072 B2, usefully returned to the processing section for isolation of crystalline methionine, as $CO_2$ was used there for neutralizing the alkaline process solution.

The liquid hydantoin-containing stream S-6 was led via a second reactor R-3, to complete the conversion. Simultaneously, entry of MMP-cyanohydrin into the hydrolysis reactor R-2 was prevented, so that disturbing formation of 4-methylmercapto-2-hydroxybutanoic acid there was prevented (see formula V). In order to minimize the energy required in the reactive distillation R-2, the hydantoin-containing process stream S-6 was preferably preheated to 130° C. by means of heat exchanger H-2 before entering at the topmost plate of the sieve-plate column R-2. On plate 1 of the reactive distillation, first any HCN still present was preferably expelled. This reduced the hydrolysis of the HCN to the potassium salt of formic acid that otherwise occurs in the alkaline in the reactive distillation (formula II).

The hydrolysis of hydantoin to methionine began with the concurrence of the hydantoin-containing process solution and stream S-8, which came from the concentrated filtrates from processing to the methionine salt solids S-9. Stream S-8 took as much heat as possible from the bottoms product of reactive distillation (heat exchanger H-4) and was thus preferably heated to 170° C. By means of evaporator unit H-5, steam was preferably produced for operation of the reactive distillation, using condensates from processing (stream S-7) as the source of water.

Via stream S-10, in particular the ammonia balance was regulated in the coupled system of the invention, because through the use of excess HCN in hydantoin synthesis and hydrolysis thereof to $NH_3$ and formic acid, additional amounts of $NH_3$ were formed, which could be withdrawn very selectively at this point, i.e. without losses of hydantoin or methionine. Evaporator H-3 produces, from boiler feed water, heating steam of pressure stage 3 bar (excess) (130° C.), which was preferably used in evaporation of the methionine mother liquor. Therefore, ideally, waste heat from the reactive distillation operated at temperatures between 170° C. and 190° C. could be used in further processing, so that the complete production process for methionine according to the method of the invention was energetically extremely favourable and therefore economically attractive.

Example 2

A sieve plate column with a diameter of 1 meter and 18 sieve plates as shown in FIG. 2 was used for continuous production of methionine. The following table shows the arrangement of the sieve plates, their spacing and weir heights:

| Plate No. | Weir height [mm] | Plate spacing [mm] |
|---|---|---|
| 1 to 5 | 150 | 1000 |
| 6 to 12 | 500 | 800 |
| 13 to 18 | 700 | 1000 |

Tank R-1 was operated with a hold-up of 3 m³, and the second reactor had a hold-up of 1 m³. Pump P-1 provided circulation of 42 t/h. At S-1, 442 kg/h HCN (16.92 kmol/h) and at S-2, 1688 kg/h MMP (16.24 kmol/h) were fed into this stream. Via S-3, a stream of 6063 kg/h with an $NH_3$ content of 11.6 wt. % of condensates from the top of the reactive distillation was mixed into the circulated process solution. Excess $CO_2$ gas (400 kg/h) left tank R-1 via a washing column, which was fed at the top (S-4) with 770 kg/h water, so that the $CO_2$ stream was washed until $NH_3$-free and could then be recycled.

By means of condenser H-1, the temperature at the outlet of R-1 was controlled at 105° C. The hydantoin reaction solution (S-6) was led through the second reactor R-3 for completing the reaction, it was heated in the heat exchanger H-2 to 130° C. and then fed at the topmost plate of the sieve plate column. 14.14 t/h of potassium carbonate-containing process solution (S-8), heated by heat exchanger H-4 to 170° C., containing the following components: 66 g/kg Met, 158 g/kg potassium, 48 g/kg Met-Met, 6.5 g/kg MHA, 12.5 g/kg formate, 3.6 mol base/kg for basicity, was pumped onto plate 2.

The stream of steam required for operation (5470 kg/h) was produced by evaporator H-5 (S-7) and was fed in below the bottommost sieve plate. From the stream distilled at the top, a partial stream S-10 (54 kg/h) was diverted and discarded.

The pressure at the top of the sieve plate column was 8.2 bar (excess) and the temperature at the inlet of the heat exchanger H-3 was 165° C. The differential pressure over all sieve plates was 450 mbar.

The temperature in the bottom of the column was 189° C.

At column outlet there was a stream S-9 of 22.15 t/h, which contains the following components: 149 g/kg Met, 32 g/kg Met-Met, 101 g/kg potassium, 8.2 g/kg formate, 4.2 g/kg MHA and with a basicity of 2.5 mol base/kg.

The sieve plate column was equipped with sampling points on plates 2, 4, 6, 8, 10, 12, 14, 16 and 18. The samples were cooled immediately and were analysed by high-performance liquid chromatography (HPLC) for hydantoin, hydantoic acid, methionine, methionyl-methionine. The $NH_3$ content was determined potentiometrically by means of an ion-selective electrode. The composition on the various sieve plates is presented in the following table and in FIG. 3.

Figure 3:
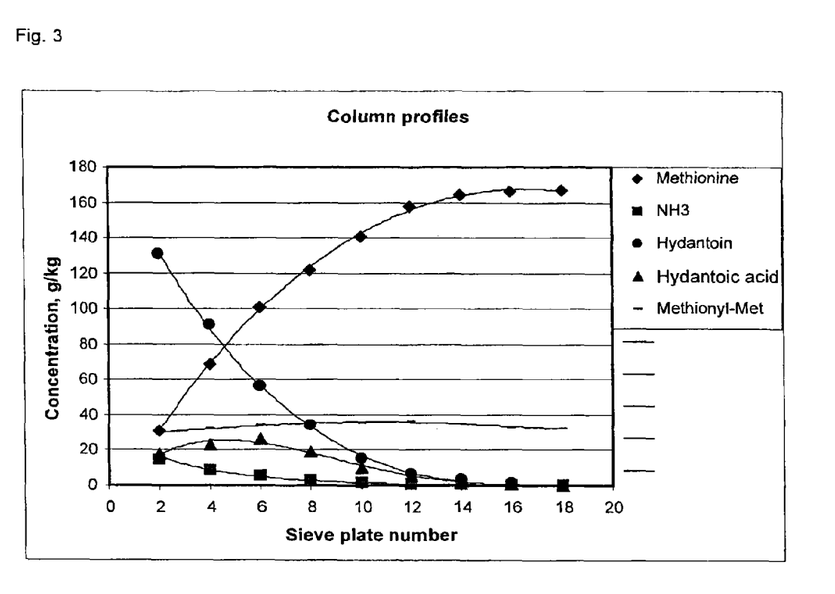
FIG. 3 shows the composition on the various sieve plates in a column of one embodiment of the invention.

| Sieve plate No. | Methionine [g/kg] | NH₃ [g/kg] | Hydantoin [g/kg] | Hydantoic acid [g/kg] | Methionyl-Met [g/kg] |
| --- | --- | --- | --- | --- | --- |
| 2 | 31 | 14.2 | 131 | 18 | 30 |
| 4 | 69 | 8.4 | 91 | 23 | 32 |
| 6 | 101 | 5 | 56 | 26 | 34 |
| 8 | 122 | 2.4 | 34 | 19 | 35 |
| 10 | 141 | 1.5 | 15.1 | 10 | 35.5 |
| 12 | 158 | 0.7 | 6.4 | 5 | 36 |
| 14 | 164 | 0.6 | 3.2 | 2.4 | 35 |
| 16 | 166 | 0.2 | 1.2 | 0.6 | 33 |
| 18 | 167 | 0.1 | 0 | 0 | 32 |

For determining the residence time, the liquids content was determined continuously, by first stopping streams S-6, S-7, S-8 and S-9 simultaneously. After waiting until no further increase in level was recorded in the column bottom, the initial level was restored in the column bottom by pumping out. The amount of solution pumped out was 2.4 t. Since the throughput in continuous operation was 22.15 t/h, this gave a residence time of the liquid phase of 6.5 min.

Numerous modifications and variations on the present invention are possible in light of the above teachings. It is therefore to be understood that within the scope of the appended claims, the invention may be practiced otherwise than as specifically described herein.

The invention claimed is:

1. A method for continuous production of a methionine salt, comprising:
    supplying a solution comprising 5-(2-methylmercaptoethyl)-hydantoin to a topmost plate of a reactive rectification column;
    conducting an alkaline hydrolysis of the 5-(2-methylmercaptoethyl)-hydantoin to obtain a methionine salt in the reactive rectification column;
    wherein an alkaline circulating solution is supplied to the reactive rectification column on a plate located under the topmost plate,
    the reactive rectification column comprises from 15 to 25 vertically stacked plates,
    each of the vertically stacked plates comprises an area permeable to a gas a downcomer and a weir separating the gas permeable area from the downcomer,
    a temperature of a gas phase at a top of the reactive-rectification column is from 160° C. to 170° C., and
    a basicity value of the methionine salt solution at a bottom outlet of the reactive rectification column is from 2.2 to 2.8 mol base per kg of the methionine salt solution.

2. The method according to claim 1, wherein the alkaline circulating solution comprises an alkali metal carbonate.

3. The method according to claim 1, further comprising:
    removing water, ammonia and $CO_2$ from the top of the reactive rectification column;
    condensing the ammonia ($NH_3$); and employing the ammonia in a synthesis of 5-(2-methylmercaptoethyl)-hydantoin.

4. The method according to claim 1, wherein a concentration of ammonia at the bottom of the rectification column is less than 120 ppm.

5. The method according to claim 1, wherein the 5-(2-methylmercaptoethyl)-hydantoin is obtained by reacting 3-methylmercaptopropionaldehyde and hydrogen cyanide in a reactive absorber and then in a second reactor.

6. The method according to claim 5, wherein the second reactor comprises a flow tube.

7. The method according to claim 1, wherein the temperature of the reaction mixture at the bottom outlet of the reactive-rectification column is from 180° C. to 190° C.

8. The method according to claim 1, a pressure of the alkaline hydrolysis is from 8 bar(excess) to 10 bar(excess).

9. The method according to claim 1, wherein a heating and stripping medium in the reactive-rectification column comprises steam.

10. The method according to claim 1,
    a height of the weir is 100 mm or more.

11. The method according to claim 1, wherein the alkaline circulating solution is fed on a 2nd vertically stacked plate from the top.

12. The method according to claim 1, wherein the alkaline circulating solution comprises potassium carbonate.

13. The method according to claim 1, further comprising removing allyl alcohol at the top of the reactive rectification column.

* * * * *